United States Patent
Hoshino et al.

(10) Patent No.: US 8,508,739 B2
(45) Date of Patent: Aug. 13, 2013

(54) GAS CONCENTRATION MEASUREMENT DEVICE

(75) Inventors: Yousuke Hoshino, Nakano-ku (JP); Kenji Takubo, Uji (JP); Naoji Moriya, Nara (JP)

(73) Assignee: Shimadzu Corporation, Kyoto (JP)

(*) Notice: Subject to any disclaimer, the term of this patent is extended or adjusted under 35 U.S.C. 154(b) by 165 days.

(21) Appl. No.: 13/189,303

(22) Filed: Jul. 22, 2011

(65) Prior Publication Data
US 2012/0188549 A1    Jul. 26, 2012

(30) Foreign Application Priority Data
Jul. 22, 2010  (JP) ................................ 2010-164767

(51) Int. Cl.
*G01N 21/59*  (2006.01)
(52) U.S. Cl.
USPC ......................................... 356/437; 356/326
(58) Field of Classification Search
USPC ......................................... 356/432–440, 326
See application file for complete search history.

(56) References Cited

U.S. PATENT DOCUMENTS

| | | | |
|---|---|---|---|
| 2004/0236195 A1* | 11/2004 | Kawaguchi et al. | 600/310 |
| 2006/0044562 A1* | 3/2006 | Hagene et al. | 356/437 |
| 2006/0262311 A1* | 11/2006 | Muta et al. | 356/437 |
| 2012/0212744 A1* | 8/2012 | Okada | 356/437 |
| 2013/0016353 A1* | 1/2013 | Gundersen et al. | 356/437 |

OTHER PUBLICATIONS

J. Reid et al., "Second-Harmonic Detection with Tunable Diode Lasers—Comparison of Experiment and Theory", Appl. Phys., B26, 1981, pp. 203-210.
Chinese Office Action dated Mar. 25, 2013 for corresponding Chinese Patent Application No. 201110209392.9, English translation of "Reason for Rejection".
Dong Feng-zhong et al., "Tunable diode laser absorption monitoring", Anhui Institute of Optics and Fine Mechanics, Chinsese Academy of Sciences, Jun. 30, 2005, 2005 Third Period, pp. 316-323. English Abstract only.

* cited by examiner

*Primary Examiner* — Hoa Pham
(74) *Attorney, Agent, or Firm* — Bingham McCutchen LLP

(57) ABSTRACT

A gas concentration measurement device which utilizes a TDLAS measurement method, and in which the phase-sensitive detection can be performed by digital processing using an integer-arithmetic device, is provided. In the gas concentration measurement device according to the present invention, AC components corresponding to integer multiples of a modulation frequency f contained in an input signal are removed by taking a moving average of data obtained from an output signal of a multiplier 62 for a period of time corresponding to one cycle of the modulation frequency f. As a result, a DC component in the output signal of a digital filter 63 relatively increases, making it easier to extract the DC component by a digital low-pass filter 64, so that a sufficiently accurate phase-sensitive detection can be made even if a digital processing based on integer arithmetic is used.

4 Claims, 4 Drawing Sheets

(A) MEASUREMENT SIGNAL (B) SIGNAL OBTAINED BY FREQUENCY CONVERSION (C) SIGNAL AFTER THE CALCULATION OF THE MOVING AVERAGE (D) SIGNAL AFTER PERFORMING THE PHASE-SENSITIVE DETECTION

INPUT TO LOCK-IN AMPLIFIER

OUTPUT FROM LOCK-IN AMPLIFIER

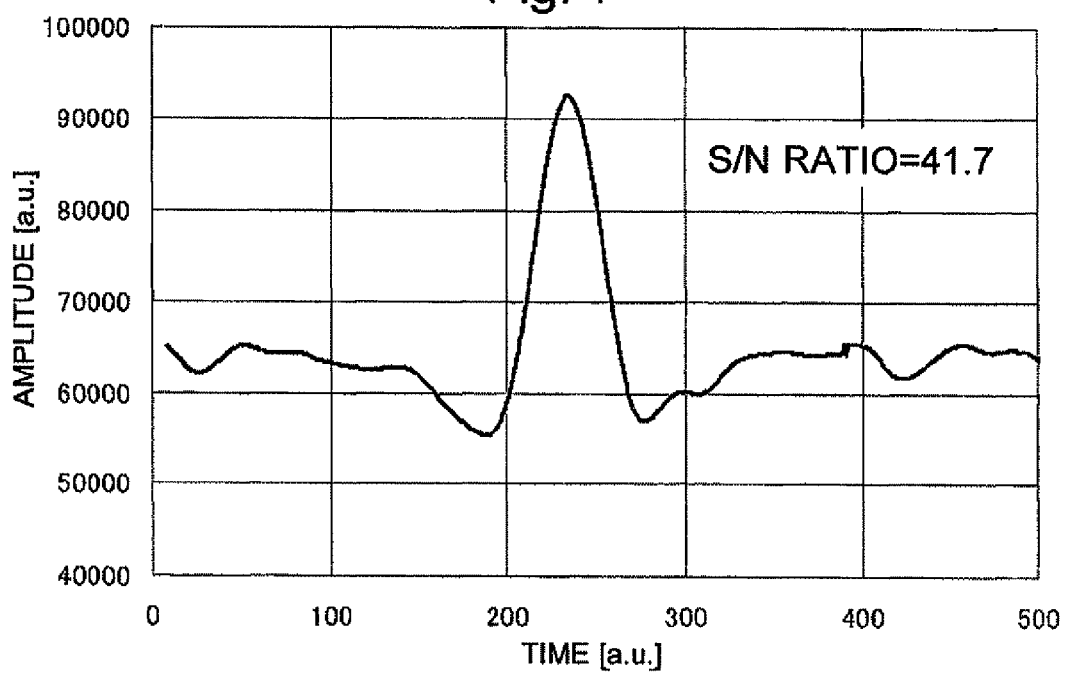

GAS CONCENTRATION MEASUREMENT DEVICE

TECHNICAL FIELD

The present invention relates to a gas concentration measurement device for measuring the concentration of a specific component contained in a gas by using absorption of laser light by the gas.

BACKGROUND ART

As one method for measuring a gas concentration, a technique called the Tunable Diode Laser Absorption Spectroscopy measurement (which is hereinafter abbreviated as the "TDLAS" measurement)

In the TDLAS measurement, a laser beam whose wavelength is modulated at frequency f is irradiated into a measurement cell containing one or more gas species to be analyzed, and the power of the laser beam that has passed through the gas is detected by a photodetector. The gas contains a variety of components, each of which absorbs light at a specific wavelength or wavelengths. Therefore, when the center of modulation wavelength is swept at a frequency sufficiently lower than the modulation frequency f, the laser beam undergoes strong absorption at around the wavelength or wavelengths characteristic of a target component of the gas. This spectral absorption line profile in the laser beam intensity is converted to a change in the amplitude of a harmonic component of the modulation frequency f. The n-fold harmonic component of the modulation frequency f (where n is an integer equal to or greater than two) contained in the output signal of the photodetector is extracted by phase-sensitive detection, and the concentration of the target component in the gas being analyzed is determined from the magnitude of the extracted component.

The TDLAS measurement is a non-contact measurement in which the photodetector and other elements do not come in contact with the gas being analyzed. Such a method has the following advantages: The measurement can be performed without disturbing the field of the gas being analyzed; the response time is extremely short and the concentration can be measured in approximately real time; and a high-sensitivity measurement is possible.

BACKGROUND ART DOCUMENT

Non-Patent Document

Non-Patent Document 1: J. Reid and D. Labrie, "Second-Harmonic Detection with Tunable Diode Lasers—Comparison of Experiment and Theory", *Appl. Phys.*, B26, 1981, pp. 203-210

DISCLOSURE OF THE INVENTION

Problem to be Solved by the Invention

The phase-sensitive detection in the TDLAS measurement is performed by the following two steps: Step 1—Multiplying the detection signal of the photodetector and a reference signal which is typically sinusoidal wave of frequency f Step 2—Integrating the product obtained by Step 1 over a predetermined time. Over these processings, the nf component in the detection signal is converted into a DC signal (i.e. a component whose frequency is around 0), while other AC (frequency) components are removed. Step 2 is performed by a low-pass filter.

Although an analogue filter may be used as the aforementioned low-pass filter, a digital filter has advantages over the analogue type in some aspects, such as higher operational speed or smaller circuit size. As the digital filter, an FIR (Finite Impulse Response) filter and an IIR (Infinite Impulse Response) filter are widely known. The FIR filter is a non-recursive filter using a predetermined number of previously sampled data. The IIR filter is a recursive filter in which the latest result of the computation is fed back to its input along with the previous data.

In the case of using a digital filter for the phase-sensitive detection, a dedicated computing device, such as a DSP (Digital Signal Processor), is employed for the filtering process. PLD (Programmable Logic Devices), such as an FPGA (Field Programmable Gate Array), is not used for this purpose. The reason is as follows.

PLDs are suitable for integer and fixed-point calculations or parallel processing but unsuitable for floating-point calculations. Therefore, although PLDs can compute faster than DSPs, the computing accuracy of the former devices is lower. In the phase-sensitive detection, the low pass filter needs an extremely steep damping property to extract the significantly small DC component of the processing signal, and a higher calculation accuracy is required. Using a PLD in the filtering process makes the computing accuracy too low to extract DC components for the TDLAS.

Performing the phase-sensitive detection using a PLD is still worth attempting since it is advantageous for increasing the operating speed of the entire device. Furthermore, PLDs are also applicable for device control and therefore allow to integrate a circuit for device control and a circuit for mathematical processing. This is advantageous for decreasing the circuit size, reducing the power consumption, and the device cost.

Therefore, the purpose to be achieved with the present invention is to provide a gas concentration measurement device utilizing a TDLAS method which can perform the digital processing only with integer-arithmetic devices.

Means for Solving the Problems

The gas concentration measurement device according to the present invention aimed at solving the aforementioned problem is a gas concentration measurement device including a laser light source for emitting laser light with a variable wavelength, a laser controller for driving the laser light source so as to modulate the wavelength of the laser light with frequency f and to let the center point (or average wavelength) of the modulation range sweep a predetermined range of laser wavelength repeatedly with a cycle period adequately longer than the cycle period of the modulation frequency f, a measurement cell into which a gas to be analyzed will be introduced, and a photodetector for detecting the laser light that has passed through the measurement cell, where the concentration of a specific component in the gas to be analyzed is determined based on a harmonic component contained in a signal produced by the photodetector, wherein the gas concentration measurement device further includes:

an A/D converter to convert an output signal from the photodetector into a digital signal;

a signal processor which generates a reference signal having a frequency nf (where n is a predetermined integer greater than one), and multiplies the above-mentioned digital converted signal and the reference signal;

a first digital filter which reduce selectively signal components of frequency mf (where m is an integer greater than zero) from the product of the above-mentioned multiplication; and a second digital filter as a low-pass filter which extracts the DC component from the output signal the above-mentioned first digital filter.

The first digital filter can be applied, for example, to a moving average of an input signal of the first digital filter (i.e. the digital signal multiplied by the reference signal) for a period of time corresponding to one cycle of the frequency f.

Effect of the Invention

The detection signal produced by the photodetector normally contains the fundamental frequency component (frequency f) with a high percentage. Production of this detection signal and a reference signal of frequency nf makes much larger amount of (n−1)f and (n+1)f components than DC component which contain gas absorbing information. Accordingly, the low pass filter which reduce these (n−1)f and (n+1)f components is required an extremely steep damping property. Interger arithmetics could not perform such as extremely steep damping property.

The gas concentration measurement device according to the present invention has solved this problem by introducing another digital filter (first digital filter) for selectively reducing an AC component having a frequency equal to the modulation frequency f before the reduction of AC components by the digital low-pass filter (second digital filter). Such a digital filter can be realized, for example, by taking a moving average of the signal over a period of time corresponding to one cycle of the frequency f. This calculation can be made with sufficient accuracy even by integer arithmetic. The preliminary reduction of the significantly contributing AC components by the additional digital filter also allows the damping property of the digital low-pass filter to be more gradual than ever before, so that the DC component can be sufficiently extracted even by integer arithmetic whose computing accuracy is rather low.

BRIEF DESCRIPTION OF THE DRAWINGS

FIG. 7 is a graph showing the result of a measurement performed using the gas concentration measurement device of the present embodiment.

BEST MODE FOR CARRYING OUT THE INVENTION

Figure 1:
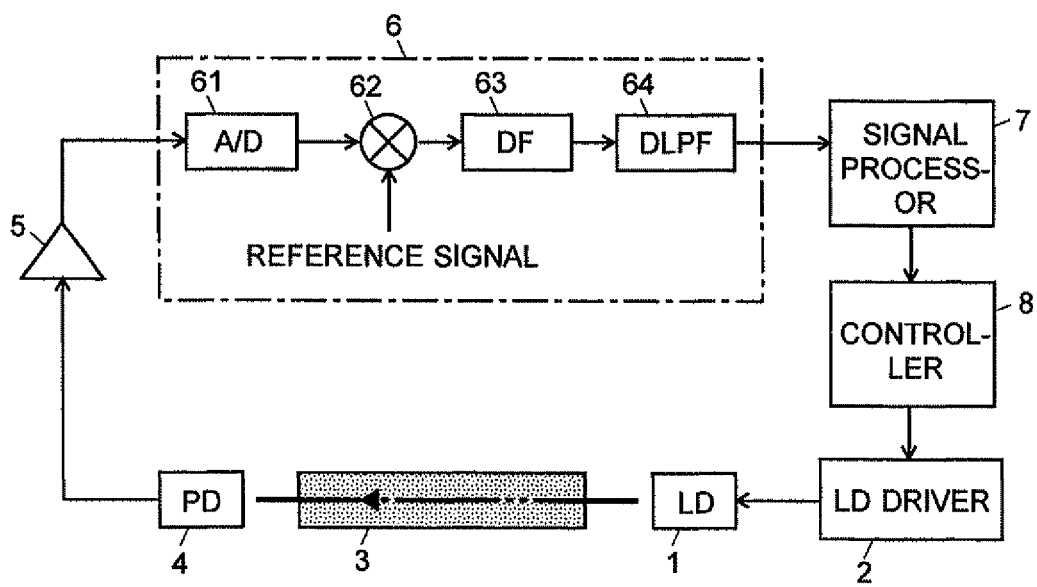
FIG. 1 is a schematic configuration diagram of a gas concentration measurement device as one embodiment of the present invention.

One embodiment of the gas concentration measurement device according to the present invention is hereinafter described with reference to the attached drawings, FIG. 1 is a schematic configuration diagram of the gas concentration measurement device according to the present embodiment.

In the gas concentration measurement device of the present embodiment, a diode laser 1 emits a laser beam whose wavelength is modulated by frequency f onto a measurement cell 3 according to a drive current supplied from a laser driver 2 under the control of a controller 8. One example of the diode laser 1 is a DFB (Distributed Feedback) laser generating a laser beam with a wavelength within the range from the near-infrared to middle-infrared region. Other types of laser may also be used.

The measurement cell 3 is contained with a gas to be analyzed. The laser beam irradiated into the measurement cell 3 undergoes absorption by the components in this gas while passing through the measurement cell 3. The laser beam that has undergone absorption reaches the photodiode (PD) 4, which generates a current signal corresponding to the intensity of the received light. The current signal is sent to a PD amplifier 5, which converts the current signal into a voltage signal and amplifies this signal. The obtained signal is sent to a lock-in amplifier 6 as a measurement signal. The lock-in amplifier 6 as a digital phase sensitive detector converts the measurement signal into a digital signal and multiplies this signal with a reference signal of a predetermined frequency to extract, from the measurement signal, only a signal component having the same frequency as that of the reference signal; and only the signal component having the same frequency as that of the reference signal is passed the two digital filters. A signal processor 7 performs a predetermined computation on the extracted signal component to calculate the concentration of a target component in the gas to be analyzed.

Figure 2:
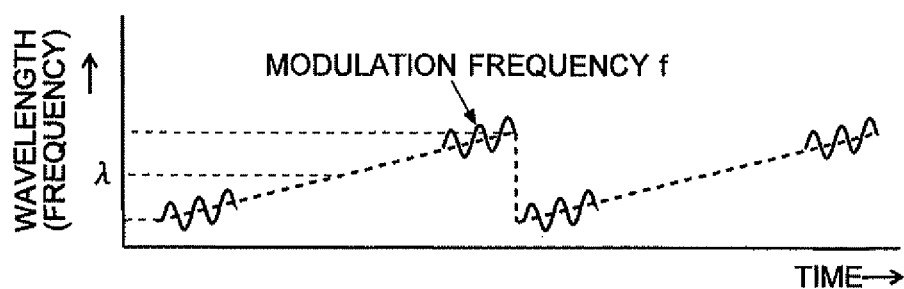
FIG. 2 is a diagram schematically showing a change in the wavelength (frequency) of a laser beam.

The measurement principle of the present gas concentration measurement device and its measurement operation are hereinafter described. The laser driver 2 supplies a drive current to the diode laser 1. This drive current is produced by adding one current for performing a modulation at a predetermined modulation frequency f and another current for repeating a wavelength sweep over a predetermined wavelength range around the absorption spectrum of a target component in the gas with a period corresponding to a frequency sufficiently lower than the modulation frequency f The diode laser 1 driven by such a current emits a frequency-modulated laser beam whose wavelength varies with time. FIG. 2 schematically shows a change in the wavelength (frequency) of the laser beam.

Before passing through the measurement cell 3, the laser beam contains only the component of modulation frequency f except for the frequency component for the wavelength sweep. In the measurement cell 3, the modulation frequency f of the laser beam is distorted due to the absorption profile with the target component in the gas, whereby harmonic components are formed. Among these harmonic components, the second harmonic component (two-fold component) normally has a waveform reflected that of an absorption peak originating from a gas component, with the peak height with wavelength sweep being proportional to the concentration of the gas component. Accordingly, the second harmonic component of the voltage signal produced by the PD amplifier 5 is extracted by the digital phase sensitive detector 6, and the concentration of the gas component is calculated from the waveform of this harmonic component change.

The detailed configuration and operation of the digital phase sensitive detector 6 are hereinafter described.

The measurement signal, which is an analogue signal produced by the PD amplifier 5, is initially sampled by an A/D converter 61 with a predetermined sampling period, to be converted into a digital signal. The digitized measurement signal is sent to a multiplier 62 and is multiplied with a reference signal of a predetermined frequency, whereby a frequency conversion as expressed by the following equation (1) is performed:

$$\sin\alpha \cdot \cos\beta = (1/2) \cdot \{\sin(\alpha+\beta) + \sin(\alpha-\beta)\} \qquad (1)$$

where $\alpha$ is the frequency of the measurement signal and $\beta$ is the frequency of the reference signal. If $\alpha=2f$ and $\beta=2f$, this equation shows that the signal obtained by the multiplication contains a component whose frequency is $4f$ and a component whose frequency is zero. The "zero-frequency" component is the DC component. That is to say, the second harmonic component of the measurement signal is frequency-converted into a DC component.

Figure 3A:
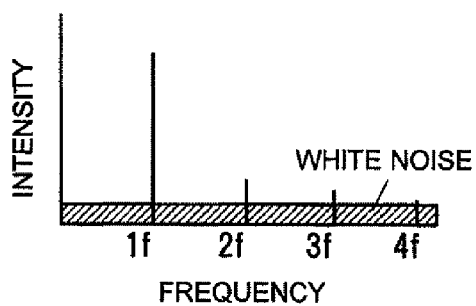
FIGS. 3A-3D are diagrams each showing one example of the frequency spectrum of (A) a measurement signal fed to an input terminal of a lock-in amplifier, (B) a signal obtained by frequency conversion, (C) a signal that have passed through a digital filter (first digital filter), or (D) a signal that have passed through a digital low-pass filter (second digital filter).
Figure 3B:
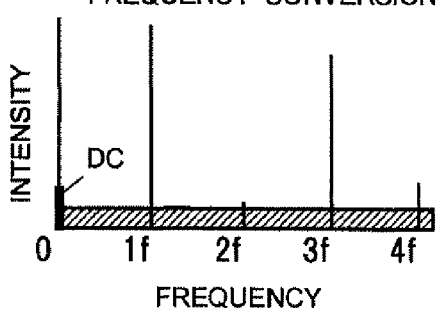

FIGS. 3A and 3B, respectively, show the frequency spectrum of a measurement signal fed to an input terminal of the digital phase sensitive detector 6 and that of a signal obtained by the frequency conversion of the measurement signal by the multiplier 62. The measurement signal shown in FIG. 3A contains a $1f$ component, which is the fundamental wave component of modulation frequency $f$, and other harmonic components as well as an AC component as a white noise.

When the measurement signal shown in FIG. 3A is multiplied by a reference signal of frequency $2f$, the $2f$ component of the measurement signal is converted into a DC component and $4f$ component shown in the frequency conversion equation (1). Similarly, the fundamental wave component having the modulation frequency $f$ is converted into two AC components with frequencies $1f$ and $3f$. The other harmonic components are also converted into AC components whose frequencies are equal to integer multiples of the modulation frequency $f$. As a result, the spectrum of the signal obtained by the frequency conversion will be as shown in FIG. 3B. As shown in FIG. 3B, the frequency-converted signal contains a DC component, AC components corresponding to integer multiples of the modulation frequency $f$, and other AC components (white noise). Therefore, to carry out a phase-sensitive detection, the AC components must be greatly reduced from the output signal of the multiplier 62 excluding the DC component.

In the case of a conventional gas concentration measurement device, the output signal of the multiplier 62 is directly processed by the digital low-pass filter to reduce the AC components. The output signal of the multiplier 62 contains AC components corresponding to integer multiples of the modulation frequency $f$, and these components have significant intensities (particularly the $1f$ and $3f$ components). Removing such components requires an extremely steep damping property. For this purpose, a high level of calculating accuracy is required.

Figure 3C:
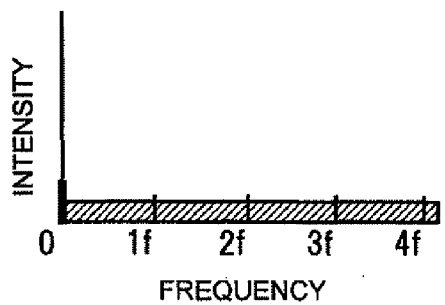

By contrast, the digital phase sensitive detector 6 in the present embodiment initially removes from the output signal of the multiplier 62 only the components corresponding to the integer multiples of the modulation frequency $f$ by using a digital filter (DF) 63. This digital filter 63 multiplies each of a plurality of input data by a specific filter factor and outputs the sum of the obtained values. In this operation, if a set of data corresponding to one cycle of the modulation frequency is used and the filter factors for the multiplication are all set to one, the result will be a moving average of the data obtained from the input signal of the digital filter 63 for a period of time corresponding to one cycle of the modulation frequency $f$. In this manner, the AC components corresponding to the integer multiples of the modulation frequency $f$ can be removed. After the calculation of the moving average, the frequency spectrum of the output signal will be as shown in FIG. 3C. This figure shows that the AC components corresponding to the integer multiples of the modulation frequency $f$ have been removed from the frequency spectrum after the calculation of the moving average, leaving the DC component and white noise.

Figure 3D:
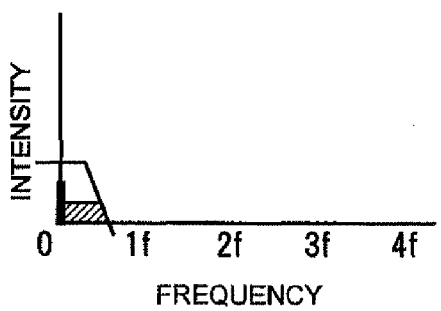

Subsequently, AC signals are removed from the output signal of the digital filter 63 by a digital low-pass filter (DLPF) 64. This digital low-pass filter should be designed to have an extremely low cut-off frequency and sufficient damping property for the sampling frequency of the A/D converter 61 so as to remove the largest possible portion of AC signals. An IIR filter will effectively function as a filter having such a property. The frequency spectrum of a signal that has passed through the digital low-pass filter 64 will be as shown in FIG. 3D. Thus, the second harmonic component of the measurement signal is extracted from the output terminal of the lock-in amplifier 6 as a DC component.

Figure 4A:
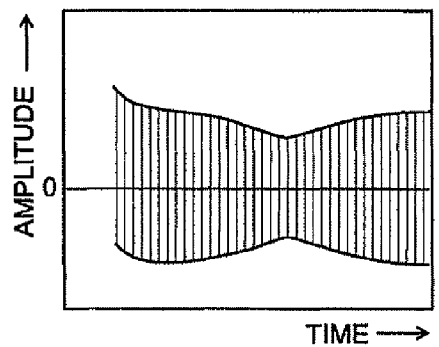
FIG. 4A is one example of a waveform diagram of a measurement signal fed to an input terminal of the lock-in amplifier.
Figure 4B:
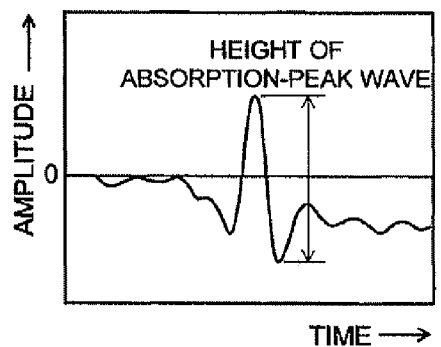
FIG. 4B is a waveform diagram of an output signal produced by the lock-in amplifier for the measurement signal shown in FIG. 4A.

FIG. 4A is one example of the waveform diagram of a measurement signal fed to the input terminal of the lock-in amplifier 6, and FIG. 4B is a waveform diagram of the output signal produced by the lock-in amplifier 6 for the measurement signal. In the measurement signal shown in FIG. 4A, only the signal of modulation frequency $f$ and the envelope of the harmonic signals thereof are noticeable, while no wave of the absorption peak due to the gas component observable is observable. On the other hand, after the components of the signals other than the second harmonic component of the modulation frequency $f$ are removed by the previously described action of the lock-in amplifier, the wave of the absorption peak becomes clearly observable, as shown in FIG. 4B.

The "peak-to-peak" height of this absorption-peak wave (which is hereinafter referred to as the "height of the absorption-peak wave") is proportional to the concentration of the target component in the gas to be analyzed. For the determination of the absolute value of the concentration of the target component, a calibration curve representing the relationship between the concentration of the target component and the height of the absorption-peak wave is created beforehand by conducting a measurement of a standard gas containing the target component with a known concentration and determining the height of the absorption-peak wave originating from that component. This calibration curve is stored in an internal memory of the signal processor 7. When a measurement of a gas containing the target component with an unknown concentration is performed and an absorption-peak wave is found, the signal processor 7 determines the height of the absorption-peak wave and refers to the calibration curve in its internal memory to calculate the concentration.

The present gas concentration measurement device assigns no specific limitation to the kinds of components to be analyzed. Although each component has a different wavelength at which it absorbs light, this difference can be handled by merely changing the wavelength range to be scanned for each target component.

As one example of the gas concentration measurement, an experiment for measuring the concentration of carbon monoxide (CO) was conducted. In this experiment, the filtering process was performed by a digital-filter system including a digital filter 63 for taking a moving average of the signal over a period of time corresponding to one cycle of the modulation frequency $f$ and an IIR-type digital low-pass filter 64. FIGS.

Figure 5:
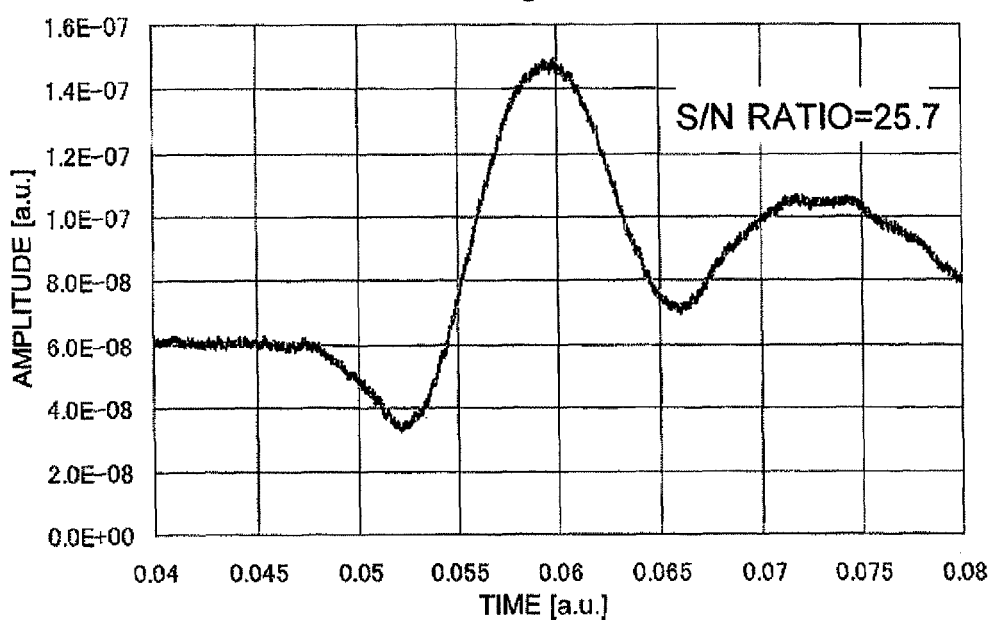
FIG. 5 is a graph showing the result of a gas concentration measurement performed using an analogue low-pass filter.
Figure 6:
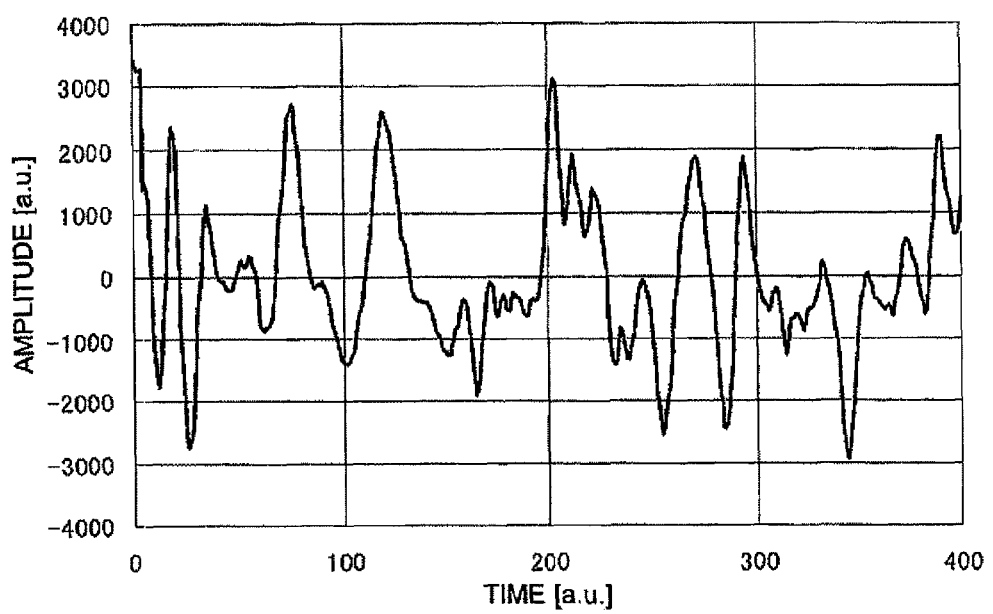
FIG. 6 is a graph showing the result of a gas concentration measurement performed using only a digital low-pass filter.

5-7 are graphs showing the results of the measurements performed by conventional methods and a method according to the present invention. More specifically, FIG. 5 shows the result of a measurement in which an analogue low-pass filter was used in the lock-in amplifier 6, FIG. 6 shows the result of a measurement in which only a digital low-pass filter was used, and FIG. 7 shows the result of a measurement in which the aforementioned digital-filter system was used. The digital processing in the examples of FIGS. 6 and 7 were performed by integer arithmetic.

An S/N ratio was defined as $S/(2\sigma)$, where S is the average of the measured values of the absorption signal and a is their standard deviation. In the case of FIG. 5, the S/N ratio was 25.7. In the case of FIG. 6, the absorption signal of the gas was totally obscured by noise and no DC component could be extracted. This is probably because the integer arithmetic lacks sufficient precision required by IIR filters. By contrast, the S/N ratio was 41.7 in the case of FIG. 7. This result demonstrates that an absorption signal of a gas can be clearly observed even when integer arithmetic is used. Furthermore, the measurement sensitivity was higher than the level achieved by the analogue processing shown in FIG. 5.

These results confirm that the method according to the present invention using a combination of the two digital filters allows the use of an integer arithmetic device in a TDLAS measurement. Furthermore, as compared to the conventional analogue processing, the present method can achieve higher S/N ratios.

If a process that corresponds to the process used in obtaining the measurement result shown in FIG. 7 is performed by a DSP, it is necessary to use 18 multipliers, with ten multipliers for the digital filter 63 and eight for the digital low-pass filter 64, for the parallel processing of the computations in the two filters. The number of multipliers included in one DSP is normally four or so. If a process to be performed by 18 multipliers is handled by a serial process using four multipliers, the processing speed of the DSP will be approximately ¼ of the frequency of the operation clock. Furthermore, the input/output of data for a DSP is also normally performed as a serial process. This means that, for an input/output of 32-bit data, the processing speed of the DSP will be as low as 1/32 of the frequency of the operation clock. Although the operation clock of recent high-grade DSPs is as high as nearly 1 GHz, the processing speed of commonly used DSPs is within the range from 200 to 300 MHz. With the aforementioned decrease in the speed due to the serial processing taken into account, the actual speed will be no higher than several MHz. By contrast, in the case of PLDs, such as FPGAs, it is easy to increase the number of multipliers according to the circuit size and arrange them in parallel. Parallel inputting/outputting of 32-bit data is also easy. Therefore, the processing speed can be as high as the frequency of the operation clock. An operation frequency of approximately 1 GHz is possible for currently available PLDs.

The TDLAS measurement is categorized as a WMS (Wavelength Modulation Spectroscopy) method, which uses a modulation frequency f of several MHz or lower, or an FMS (Frequency Modulation Spectroscopy) method, which uses an extremely high frequency of 10 MHz to several GHz. The EMS method using the higher frequency band is capable of a measurement with higher sensitivity free from the influence of the 1/f noise. Processing high-frequency signals requires an operation at higher speeds. Therefore, the filtering method according to the present invention, which allows the use of a PLD, has an evident advantage over the method using a DSP.

In the TDLAS measurement, the measurement conditions may be slightly changed depending on the kind of the gas to be measured. To deal with this situation, an easy modification and/or addition of a program is desirable. FPGA, which is a type of PLD, allows the modification or addition of a program to be easily made, and therefore is more suitable for the TDLAS measurement than the DSP.

PLDs can be used for not only the phase-sensitive detection but also the entire control of the device to improve the efficiency of the system and decrease the size of the circuit board. Furthermore, PLDs allow the use of integer arithmetic for the TDLAS measurement, which is advantageous for increasing the measurement speed and decreasing the power consumption.

It should be noted that any of the previous embodiments is a mere example of the present invention, and any change, modification or addition appropriately made within the spirit of the present invention will evidently fall within the scope of claims of the present patent application.

EXPLANATION OF NUMERALS

1 . . . Diode Laser
2 . . . Laser Driver
3 . . . Measurement Cell
4 . . . Photodiode (PD)
5 . . . PD Amplifier
6 . . . Lock-in Amplifier
61 . . . A/D Converter
62 . . . Multiplier
63 . . . Digital Filter (First Digital Filter)
64 . . . Digital Low-Pass Filter (Second Digital Filter)
7 . . . Signal Processor
8 . . . Controller

The invention claimed is:

1. A gas concentration measurement device including a laser light source for emitting laser light with a variable wavelength, a laser controller for driving the laser light source so as to modulate the wavelength of the laser light with a frequency f and to let a center point of the modulation range sweep a predetermined wavelength range repeatedly at a frequency lower than the frequency f, a measurement cell into which a gas to be analyzed will be introduced, and a photodetector for detecting the laser light that has passed through the measurement cell, where a concentration of a specific component in the gas to be analyzed is determined based on a harmonic component contained in a signal produced by the photodetector, the gas concentration measurement device comprising:
   an A/D converter for converting an output signal from the photodetector into a digital signal;
   a signal processor for generating a reference signal having a frequency nf (where n is a predetermined integer greater than one), and for multiplying the digital signal converted by the A/D converter and the reference signal;
   a first digital filter for reducing selectively signal component of frequency mf (where m is an integer greater than zero) from the product of the multiplication by the signal processor; and
   a second digital filter as a low-pass filter for extracting a direct-current component from the output signal of the first digital filter.

2. The gas concentration measurement device according to claim 1, wherein the first digital filter takes a moving average of the digital signal multiplied by the reference signal for a period of time corresponding to one cycle of the frequency f.

3. The gas concentration measurement device according to claim 2, wherein filtering processes by the first digital filter and the second digital filter are performed by integer arithmetic.

4. The gas concentration measurement device according to claim 1, wherein filtering processes by the first digital filter and the second digital filter are performed by integer arithmetic.

* * * * *